(12) United States Patent
Biederer et al.

(10) Patent No.: US 9,084,552 B2
(45) Date of Patent: Jul. 21, 2015

(54) APPARATUS AND METHOD FOR INFLUENCING AND/OR DETECTING MAGNETIC PARTICLES

(75) Inventors: Sven Biederer, Luebeck (DE); Timo Frederik Sattel, Luebeck (DE); Tobias Knopp, Luebeck (DE); Thorsten Manuel Buzug, Gross Sarau (DE)

(73) Assignee: Koninklijke Philips N.V., Eindhoven (NL)

( * ) Notice: Subject to any disclaimer, the term of this patent is extended or adjusted under 35 U.S.C. 154(b) by 535 days.

(21) Appl. No.: 13/392,220

(22) PCT Filed: Sep. 6, 2010

(86) PCT No.: PCT/IB2010/053995
§ 371 (c)(1),
(2), (4) Date: Feb. 24, 2012

(87) PCT Pub. No.: WO2011/030275
PCT Pub. Date: Mar. 17, 2011

(65) Prior Publication Data
US 2012/0153949 A1    Jun. 21, 2012

(30) Foreign Application Priority Data
Sep. 11, 2009 (EP) .................. 09170076

(51) Int. Cl.
*A61B 5/05* (2006.01)
*A61N 2/02* (2006.01)
(52) U.S. Cl.
CPC .............. *A61B 5/05* (2013.01); *A61B 5/0515* (2013.01); *A61N 2/02* (2013.01)

(58) Field of Classification Search
CPC ............. A61B 5/05; A61B 5/0515; A61N 2/02
USPC .................................................. 324/300–322
See application file for complete search history.

(56) References Cited

U.S. PATENT DOCUMENTS

2008/0204009 A1    8/2008   Gleich et al.

FOREIGN PATENT DOCUMENTS

| | | |
|---|---|---|
| DE | 10151778 | 5/2003 |
| EP | 1304542 | 4/2003 |
| WO | 2004091386 | 10/2004 |
| WO | 2004091390 | 10/2004 |
| WO | 2004091394 | 10/2004 |
| WO | 2004091395 | 10/2004 |
| WO | 2004091396 | 10/2004 |
| WO | 2004091397 | 10/2004 |

(Continued)

OTHER PUBLICATIONS

B. Gleich, et al., "Tomographic Imaging using the Nonlinear Response of Magnetic Particles", Nature, vol. 435, Jun. 30, 2005; doi: 10/1038, pp. 1214-1217.

(Continued)

*Primary Examiner* — Dixomara Vargas (57) ABSTRACT

The present invention relates to an MPI (Magnetic Particle Imaging) apparatus and a method for influencing and/or detecting magnetic particles in a field of view. Rather than moving the FFP (field free point) along a single, time-consuming high density trajectory it is proposed to use a number of low density trajectories with travelling phase, wherein each of said low density trajectories has the form of a closed curve differently located within the field of view.

11 Claims, 9 Drawing Sheets

(56) References Cited

FOREIGN PATENT DOCUMENTS

| WO | 2004091398 | 10/2004 |
| WO | 2004091408 | 10/2004 |
| WO | 2008078244 | 7/2008 |

OTHER PUBLICATIONS

T. Knopp, et al., "Trajectory Analysis for Magnetic Particle Imaging", Physics in Medicine and Biology, 54 (2009), pp. 385-397.

J. Rahmer, et al., "Signal Encoding in Magnetic Particle Imaging: Properties of the System Function", BMC Medical Imaging 2009, 9 4, pp. 1-21.

APPARATUS AND METHOD FOR INFLUENCING AND/OR DETECTING MAGNETIC PARTICLES

FIELD OF THE INVENTION

The present invention relates to an apparatus and a method for influencing and/or detecting magnetic particles in a field of view. Further, the present invention relates to a computer program for implementing said method on a computer and for controlling such an apparatus.

BACKGROUND OF THE INVENTION

Magnetic Particle Imaging (MPI) is an emerging medical imaging modality. The first versions of MPI were two-dimensional in that they produced two-dimensional images. Future versions will be three-dimensional (3D). A time-dependent, or 4D, image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called "selection field", which has a single field free point (FFP) at the isocenter of the scanner. In addition, the scanner has means to generate a time-dependent, spatially nearly homogeneous magnetic field. Actually, this field is obtained by superposing a rapidly changing field with small amplitude, called "drive field", and a slowly varying field with a large amplitude, called "focus field". By adding the time-dependent drive and focus fields to the static selection field, the FFP may be moved along a predetermined FFP trajectory throughout a volume of scanning surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles; if the object is an animal or a patient, a contrast agent containing such particles is administered to the animal or patient prior to the scan. During the data acquisition, the MPI scanner steers the FFP along a deliberately chosen trajectory that traces out the volume of scanning, or at least the field of view. The magnetic nanoparticles within the object experience a changing magnetic field and respond by changing their magnetization. The changing magnetization of the nanoparticles induces a time dependent voltage in each of the receive coils. This voltage is sampled in a receiver associated with the receive coil. The samples output by the receivers are recorded and constitute the acquired data. The parameters that control the details of the data acquisition make up the scan protocol.

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model is an integral operator that acts on the acquired data; the reconstruction algorithm tries to undo, to the extent possible, the action of the model.

Such an MPI apparatus and method have the advantage that they can be used to examine arbitrary examination objects— e.g. human bodies—in a non-destructive manner and without causing any damage and with a high spatial resolution, both close to the surface and remote from the surface of the examination object. Such an arrangement and method are generally known and are first described in DE 101 51 778 A1 and in Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication take advantage of the non-linear magnetization curve of small magnetic particles.

In the paper of T. Knopp et al. "Trajectory analysis for magnetic particle imaging", Phys. Med. Biol. 54 (2009) 385-397, a simulation study is performed on different trajectories moving the field-free point through the field of view. The purpose is to provide mandatory information for the design of a magnetic particle imaging scanner. Trajectories are compared with respect to density, speed and image quality when applied in data acquisition. In particular, a Lissajous trajectory was compared to four other trajectory types. Overall, the Lissajous trajectory yielded excellent image quality and outperformed the Cartesian and spiral sampling patterns. In practice, the Lissajous trajectory and the Cartesian trajectory can be realized with only two dedicated frequencies. This has the advantage that the signals for both drive field coils can be band-pass filtered to compensate for harmonic distortions of available amplifiers.

With the known MPI apparatus and method the trajectory for moving the FFP is fixed, mainly because the slightly different transmit frequencies used for realizing the Lissajous trajectory are fixed due to the resonance matching of the drive coils and the respective filter used in a drive field signal generator. This results in a fixed resolution and repetition time. Generally, a high resolution is desired for which purpose generally a dense Lissajous trajectory is applied using high transmit frequencies which are only slightly different.

SUMMARY OF THE INVENTION

It is an object of the present invention to provide an apparatus and a method for influencing and/or detecting magnetic particles in a field of view which allow for changing the sampling trajectory and the resulting resolution without hardware modification.

It is a further object of the present invention to provide a computer program for implementing said method on a computer and for controlling such an apparatus.

In a first aspect of the present invention an apparatus for influencing and/or detecting magnetic particles in a field of view is presented comprising:

selection means comprising a selection field signal generator unit and selection field elements for generating a magnetic selection field having a pattern in space of its magnetic field strength such that a first sub-zone having a low magnetic field strength and a second sub-zone having a higher magnetic field strength are formed in the field of view, drive means comprising drive field signal generator units and drive field coils for changing the position in space of the two sub-zones in the field of view by means of a magnetic drive field so that the magnetization of the magnetic material changes locally, and control means for controlling said drive field signal generator units to generate drive currents for causing the drive field coils to generate a magnetic drive field such that the first sub-zone moves along a number p of predetermined low density trajectories each having the form of a closed curve differently located within the field of view, wherein each drive current has a drive current frequency and a drive current phase, wherein the drive currents are generated such that their drive current frequencies are equal or have a frequency ratio in the range from 0.5 to 0.98 and that the drive current phases of at least one drive current are different for the plurality p of low density trajectories, resulting in a high density sampling of the field of view by said first sub-zone after movement along said number p of predetermined low density trajectories.

In a further aspect of the present invention a corresponding method is presented.

Preferred embodiments of the invention are defined in the dependent claims. It shall be understood that the claimed method and the claimed computer program have similar and/or identical preferred embodiments as the claimed apparatus and as defined in the dependent claims.

The present invention is based on the idea not to use a single fixed trajectory for moving the FFP through the field of view and sampling it with high density, but to use low density trajectories, which are moving the FFP through the field of view along different paths so that, finally, the field of view is sampled with a desired density, for instance with the same high density as with the known single Lissajous trajectory. To achieve this, for instance, the same low density trajectory is used, but with different phases.

The density and the spatial displacement of the used low density trajectories can be controlled by the drive current frequency and the drive current phase of the drive currents provided to the drive coils for generating the required (homogeneous) magnetic drive fields. Hence, by an appropriate control of the drive current frequency and the drive current phase of the drive currents through a control unit the magnetic drive fields and, thus, the path of the FFP through the field of view can be controlled. Hence, for choosing (and changing) the sampling density, variation of the repetition time for a trajectory and the form and path of the trajectory within the field of view no major hardware modification (or no hardware modification at all) is necessary.

In this mode the drive current frequencies have a frequency ratio in the range from 0.5 to 0.98, which means that the trajectory is a low density trajectory since trajectories having a frequency ratio above 0.98 are considered to be a high density trajectory.

The invention also allows to use identical drive current frequencies for all (two or three) drive currents, i.e. for all imaging directions and to vary the phase differences between the drive currents after each trajectory to change the form and path of the trajectory within the field of view. The use of the same drive current frequencies has the advantage that less tuning (particularly only once) of filters and amplifiers is required compared to the situation using different drive current frequencies.

The invention provides the further advantage that, for instance, a single low density trajectory can be used for making a single (fast) low density scan, and that subsequently, e.g. for a desired region, a (slow) high density scan is made, e.g. by using a plurality of low density trajectories with modified drive current phases from one trajectory to the next trajectory or using a single (conventional) high density trajectory.

Although generally, any kind of trajectory having any kind of form can be used to form a closed curve can be applied, according to a preferred embodiment the drive currents are orthogonal sinusoidal drive currents, and the trajectories have particularly the form of Lissajous curves. Such drive currents and trajectories, respectively, can be easily generated and modified, e.g. controlled by a user or preset, and easily allow control of the sampling density, preferably with rather uniformly distributed sampling points.

Preferably, the drive currents $I_i$ are of the form $I_i = \hat{I}_i \sin(2\pi f_i t + \phi_i)$, wherein $\hat{I}_i$ is the drive current amplitude, $\phi_i$ is the drive current phase, $f_i$ is drive field frequency and i indicates the direction of the magnetic drive field caused by the drive field coil provided with drive current $I_i$, wherein the drive current frequencies $f_i$ are all equal or wherein the drive current frequencies $$\frac{f_1}{f_2}$$

have a first frequency ratio of $$\frac{N-1}{N}$$

and the drive current frequencies $$\frac{f_3}{f_1}$$

have a second frequency ratio of $$\frac{N}{N+1},$$

N being a positive integer smaller than 50, in particular smaller than 20. Thus, simply by selection of the parameter N the density can be selected.

The number p of predetermined low density trajectories is preferably larger than 2, in particular larger than 10, more preferably in the range from 10 to 200, in particular in the range from 50 to 100.

According to another embodiment the drive current phases $\phi_i$ of at least one drive current $I_i$ are distributed, in particular equally distributed, over the phase range from 0° to 360° for the number p of predetermined low density trajectories. The equal distribution has the advantage that the area of interest is equally dense sampled.

Depending on the kind of application and use of the apparatus according to the present invention further, generally known means may be provided, such as focus means comprising a focus field signal generator unit and focus field coils for changing the position in space of the field of view by means of a magnetic focus field; and/or receiving means comprising at least one signal receiving unit and at least one receiving coil for acquiring detection signals, which detection signals depend on the magnetization in the field of view, which magnetization is influenced by the change in the position in space of the first and second sub-zone, and processing means for processing said detection signals, in particular for reconstructing an image from said detection signals and/or for localizing said magnetic particles within the field of view, in particular within an object placed within the field of view.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 4. In particular, two embodiments of an MPI scanner for medical diagnostics will be described. An informal description of the data acquisition is also given. The similarities and differences between the two embodiments will be pointed out.

Figure 1:
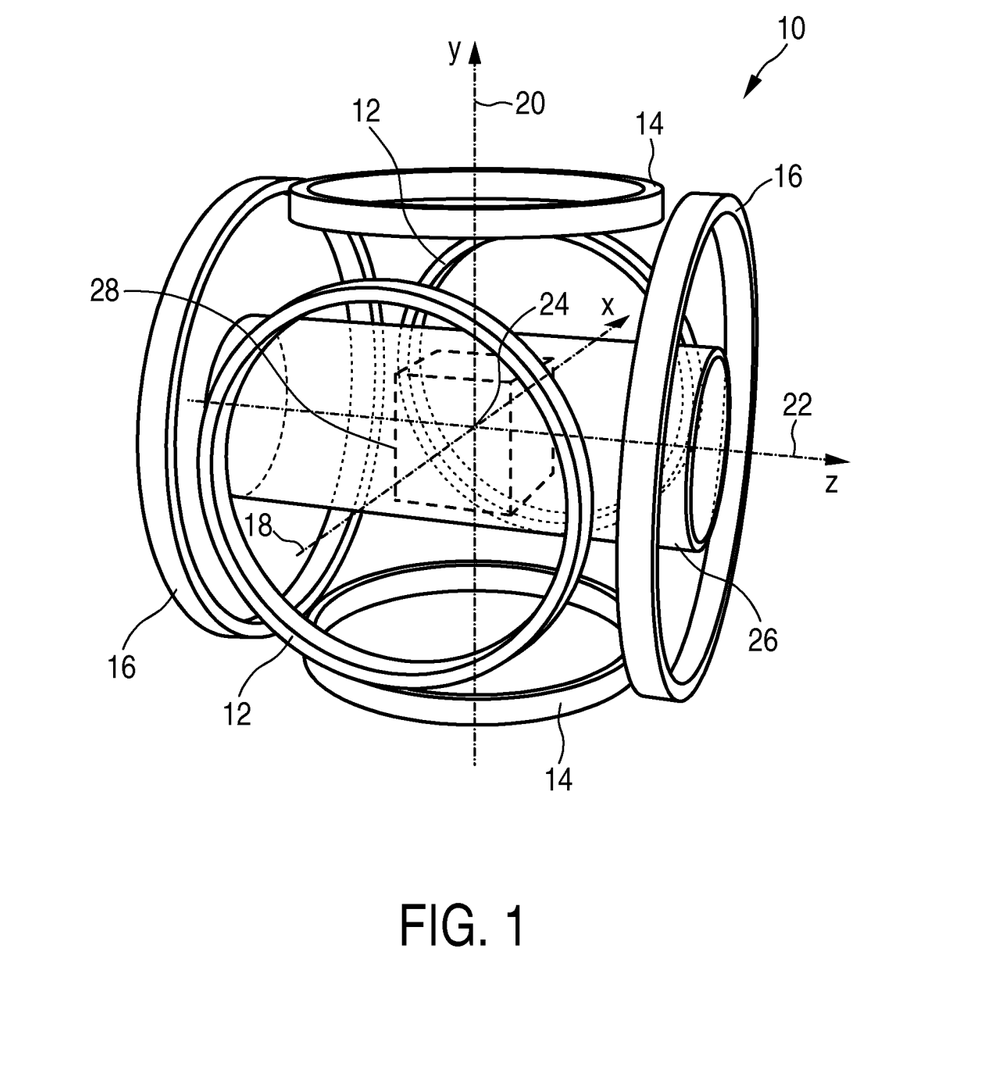
FIG. 1 shows a first embodiment of an MPI apparatus.

The first embodiment 10 of an MPI scanner shown in FIG. 1 has three prominent pairs 12, 14, 16 of coaxial parallel circular coils, each pair being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x and z-axes are horizontal. The coil pairs 12, 14, 16 are also named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils.

The scanner 10 can be set to direct a predetermined, time dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current $-I^S$ is made to flow through the $z^-$-coil. The z-coil pair 16 then acts as an anti-parallel circular coil pair.

Figure 2:
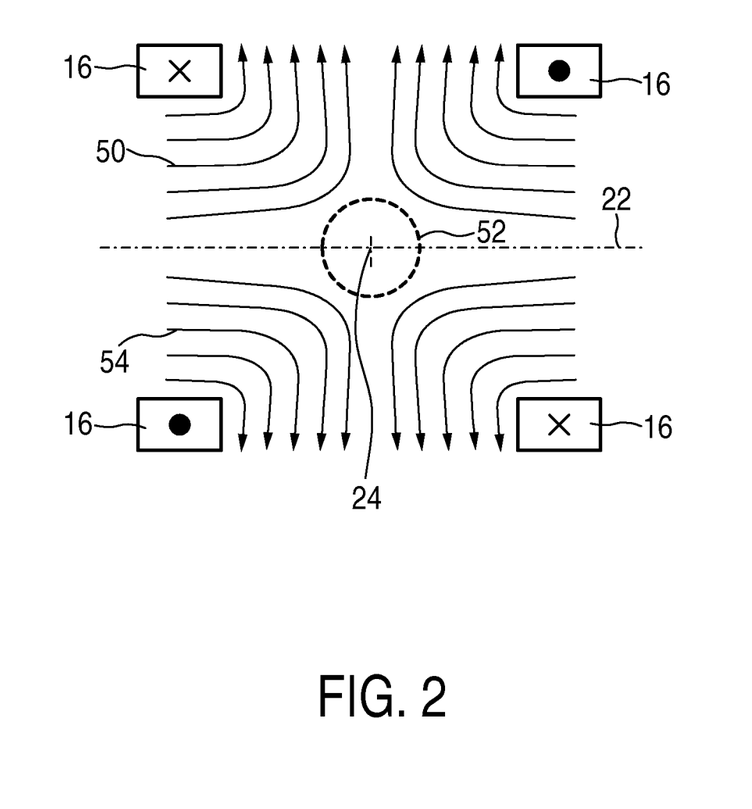
FIG. 2 shows an example of the selection field pattern produced by an apparatus as shown in FIG. 1.

The magnetic selection field which is generally a gradient magnetic field is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. The field-free point or first sub-zone 52 of the scanner's field of view 28 is preferably a spatially coherent area; it may also be a punctiform area, a line or a flat area. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 within the field of view 28, the (overall) magnetization in the field of view 28 changes. By measuring the magnetization in the field of view 28 or physical parameters influenced by the magnetization, information about the spatial distribution of the magnetic particles in the field of view 28 can be obtained. In order to change the relative spatial position of the two sub-zones 52, 54 in the field of view 28, further magnetic fields, i.e. the magnetic drive field, and, if applicable, the magnetic focus field, are superposed to the selection field 50 in the field of view 28 or at least in a part of the field of view 28.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field. The current flowing through the $z^\pm$-coil is $I^D_3+I^F_3+I^S$. The current flowing through the remaining two coil pairs 12, 14 is $I^D_k+I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time dependent. The difference between the focus field and the drive field is that the focus field varies slowly in time and has a large amplitude while the drive field varies rapidly and has a small amplitude. There are physical and biomedical reasons to treat these fields differently. A rapidly varying field with a large amplitude would be difficult to generate and hazardous to the patient.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from DC up to the point where the expected signal level drops below the noise level.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged (or treated) is placed in the bore 26 such that the patient's volume of interest—that volume of the patient (or object) that shall be imaged (or treated)—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, or a cylinder. A cubical field of view 28 is illustrated in FIG. 1.

The size of the first sub-zone 52 is dependent on the one hand on the strength of the gradient of the magnetic selection field and on the other hand on the field strength of the magnetic field required for saturation. For a sufficient saturation of the magnetic particles at a magnetic field strength of 80 A/m and a gradient (in a given space direction) of the field strength of the magnetic selection field amounting to $50 \times 10^3$ A/m$^2$, the first sub-zone 52 in which the magnetization of the particles is not saturated has dimensions of about 1 mm (in the given space direction).

The patient's volume of interest is supposed to contain magnetic nanoparticles. Especially prior to a therapeutic and/or diagnostic treatment of, for example, a tumor, the magnetic particles are positioned in the volume of interest, e.g. by means of a liquid comprising the magnetic particles which is injected into the body of the patient (object) or otherwise administered, e.g. orally, to the patient.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating of a material having a lower saturation magnetization is chosen or when the thickness of the layer is reduced. Magnetic particles that can generally be used are available on the market under the trade name Resovist.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

The data acquisition starts at time $t_s$ and ends at time $t_e$. During the data acquisition, the x-, y-, and z-coil pairs 12, 14, 16 generate a position- and time dependent magnetic field, the applied field. This is achieved by directing suitable currents through the coils. In effect, the drive and focus fields push the selection field around such that the FFP moves along a pre-selected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time dependent voltage $V_k$ across the terminals of receive coil pair along the $x_k$-axis. The associated receiver converts this voltage to a signal $S_k(t)$, which it samples and outputs.

It is advantageous to receive or to detect signals from the magnetic particles located in the first sub-zone 52 in another frequency band (shifted to higher frequencies) than the frequency band of the magnetic drive field variations. This is possible because frequency components of higher harmonics of the magnetic drive field frequency occur due to a change in magnetization of the magnetic particles in the scanner's field of view 28 as a result of the non-linearity of the magnetization characteristics.

Figure 3:
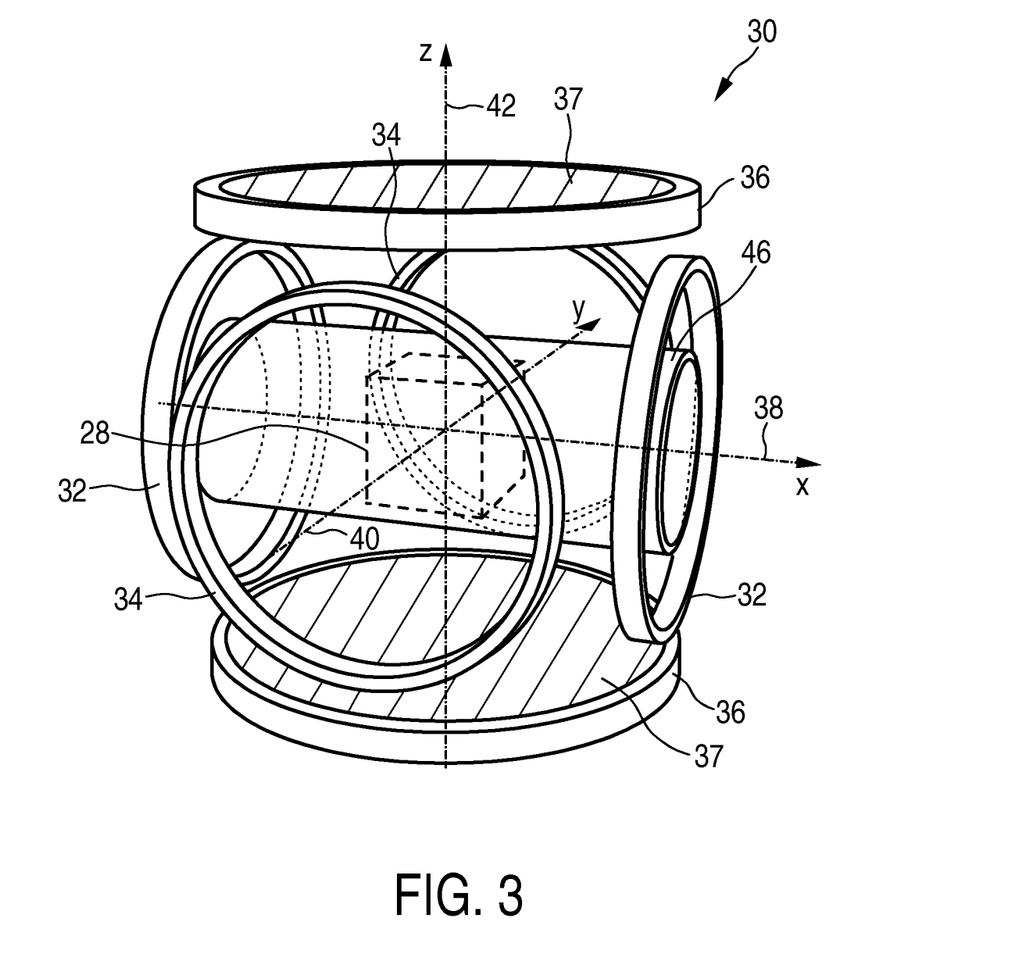
FIG. 3 shows a second embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils. The signals picked up by the receive coils are sent through a high-pass filter that suppresses the contribution caused by the applied field.

To give a few typical parameters of such an embodiment: The z-gradient of the selection field, G, has a strength of $G/\mu_0=2.5$ T/m, where $\mu_0$ is the vacuum permeability. The selection field generated does either not vary at all over the time or the variation is comparably slow, preferably between approximately 1 Hz and approximately 100 Hz. The temporal frequency spectrum of the drive field is concentrated in a narrow band around 25 kHz (up to approximately 100 kHz). The useful frequency spectrum of the received signals lies between 50 kHz and 1 MHz (eventually up to approximately 10 MHz). The bore has a diameter of 120 mm. The biggest cube 28 that fits into the bore 46 has an edge length of 120 mm/$\sqrt{2}\approx$84 mm.

As shown in the above embodiments the various magnetic fields can be generated by coils of the same coils pairs and by providing these coils with appropriately generated currents. However, and especially for the purpose of a signal interpretation with a higher signal to noise ratio, it may be advantageous when the temporally constant (or quasi constant) selection field and the temporally variable drive field and focus field are generated by separate coil pairs. Generally, coil pairs of the Helmholtz type can be used for these coils, which are generally known, e.g. from the field of magnetic resonance apparatus with open magnets (open MRI) in which a radio frequency (RF) coil pair is situated above and below the region of interest, said RF coil pair being capable of generating a temporally variable magnetic field. Therefore, the construction of such coils need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4:
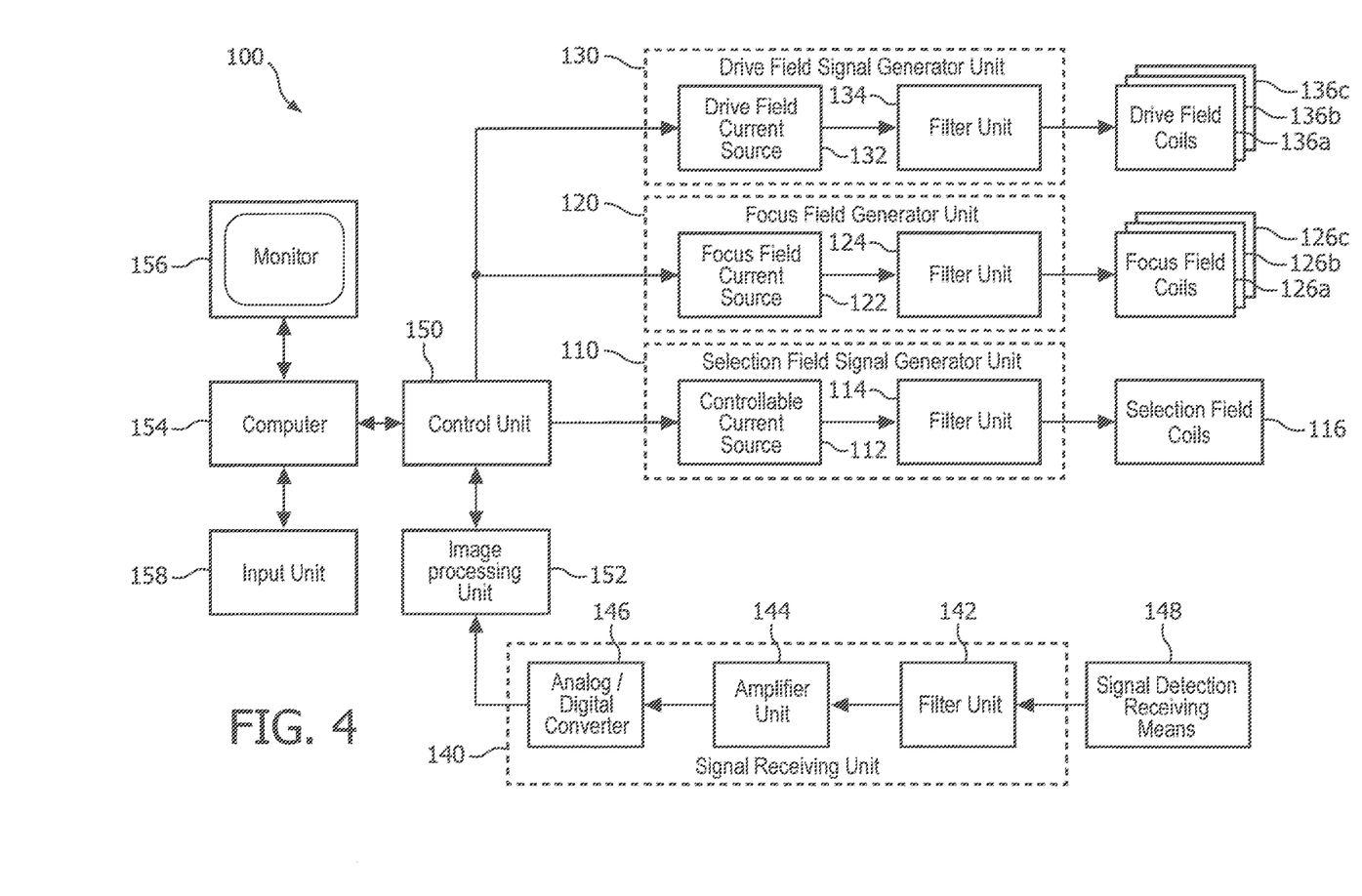
FIG. 4 shows a block diagram of an MPI apparatus according to the present invention.

FIG. 4 shows a general block diagram of an MPI apparatus 10 according to the present invention. The general principles of magnetic particle imaging and of magnetic resonance imaging explained above are valid and applicable to this embodiment as well, unless otherwise specified.

The embodiment of the apparatus 100 shown in FIG. 4 comprises a set of various coils for generating the desired magnetic fields. First, the coils and their functions in a MPI mode shall be explained.

For generating the magnetic (gradient) selection field explained above, selection means are provided comprising a set of selection field (SF) coils 116, preferably comprising at least one pair of coil elements. The selection means further comprises a selection field signal generator unit 110. Preferably, a separate generator subunit is provided for each coil element (or each pair of coil elements) of the set 116 of selection field coils. Said selection field signal generator unit 110 comprises a controllable selection field current source 112 (generally including an amplifier) and a filter unit 114 which provide the respective section field coil element with the selection field current to individually set the gradient strength of the selection field in the desired direction. Preferably, a DC current is provided. If the selection field coil elements are arranged as opposed coils, e.g. on opposite sides of the field of view, the selection field currents of opposed coils are preferably oppositely oriented.

The selection field signal generator unit 110 is controlled by a control unit 150, which preferably controls the selection field current generation 110 such that the sum of the field strength and the sum of the gradient strength of all spatial fractions of the selection field is maintained at a predefined level.

For generation of a magnetic focus field the apparatus 100 further comprises focus means comprising a set of focus field (FF) coils, preferably comprising three pairs 126a, 126b, 126c of oppositely arranged focus field coil elements. Said magnetic focus field is generally used for changing the position in space of the region of action. The focus field coils are controlled by a focus field signal generator unit 120, preferably comprising a separate focus field signal generation subunit for each coil element (or at least each pair of coil elements) of said set of focus field coils. Said focus field signal generator unit 120 comprises a focus field current source 122 (preferably comprising a current amplifier) and a filter unit 124 for providing a focus field current to the respective coil of said subset of coils 126a, 126b, 126c which shall be used for generating the magnetic focus field. The focus field current unit 120 is also controlled by the control unit 150.

For generation of the magnetic drive field the apparatus 100 further comprises drive means comprising a subset of drive field (DF) coils, preferably comprising three pairs 136a, 136b, 136c of oppositely arranged drive field coil elements. The drive field coils are controlled by a drive field signal generator unit 130, preferably comprising a separate drive field signal generation subunit for each coil element (or at least each pair of coil elements) of said set of drive field coils. Said drive field signal generator unit 130 comprises a drive field current source 132 (preferably including a current amplifier) and a filter unit 134 for providing a drive field current to the respective drive field coil. The drive field current source 132 is adapted for generating an AC current and is also controlled by the control unit 150.

For signal detection receiving means 148, in particular a receiving coil, and a signal receiving unit 140, which receives signals detected by said receiving means 148, are provided. Said signal receiving unit 140 comprises a filter unit 142 for filtering the received detection signals. The aim of this filtering is to separate measured values, which are caused by the magnetization in the examination area which is influenced by the change in position of the two part-regions (52, 54), from other, interfering signals. To this end, the filter unit 142 may be designed for example such that signals which have temporal frequencies that are smaller than the temporal frequencies with which the receiving coil 148 is operated, or smaller than twice these temporal frequencies, do not pass the filter unit 142. The signals are then transmitted via an amplifier unit 144 to an analog/digital converter 146 (ADC). The digitalized signals produced by the analog/digital converter 146 are fed to an image processing unit (also called reconstruction means) 152, which reconstructs the spatial distribution of the magnetic particles from these signals and the respective position which the first part-region 52 of the first magnetic field in the examination area assumed during receipt of the respective signal and which the image processing unit 152 obtains from the control unit 150. The reconstructed spatial distribution of the magnetic particles is finally transmitted via the control means 150 to a computer 154, which displays it on a monitor 156. Thus, an image can be displayed showing the distribution of magnetic particles in the field of view of the examination area.

Further, an input unit 158 is provided, for example a keyboard. A user is therefore able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154. The control unit 150 in this embodiment sets the gradient field in a first direction which is automatically estimated or set as start value by the user. The direction of the gradient field is then varied stepwise until the resolution of the thereby received images, which are compared by the computer 154, is maximal, respectively not improved anymore. The most critical direction can therefore be found respectively adapted automatically in order to receive the highest possible resolution.

According to the present invention the control unit 150 is adapted for controlling said drive field signal generator unit 130, in particular the drive current source 132, such that it generates drive currents for causing the drive field coils 136a, 136b, 136c to generate a magnetic drive field such that the first sub-zone 52 moves along a number p of predetermined low density trajectories each having the form of a closed curve differently located within the field of view 28. Each drive current has a drive current frequency and a drive current phase, and the drive currents are generated such that their drive current frequencies are equal or have a frequency ratio in the range from 0.5 to 0.98 and that the drive current phases of at least one drive current are different for the plurality p of low density trajectories, resulting in a high density sampling of the field of view by said first sub-zone after movement along said number p of predetermined low density trajectories.

In other words, according to the present invention, the field of view is not sampled by moving the FFP along a single high density trajectory, but the sampling is not by use of more than one low density trajectories which are each sampling the field of view along different paths, so that the subsequent movement of the FFP along said low density trajectories results finally in a high density sampling as well. Compared to the known method, the control proposed according to the present invention provides a higher flexibility to the user, e.g. to select the desired resolution and the available scan time.

The trajectory used according to a preferred embodiment of the present invention has the form of a closed Lissajous curve having a low density. For moving the FFP along a defined trajectory or for changing the position in space of the first sub-zone 52 along a defined trajectory a sequence of varying currents has to flow in the drive field coils 136a, 136b, 136c. In case of a 2D Lissajous curve two of the drive field coils 136a, 136b, 136c are controlled with sinusoidal drive field currents. The 2D Lissajous curve is generated by superposition of two orthogonal harmonic drive fields. For instance a first drive field coil generating a magnetic drive field in direction of the x-axis and a second drive field coil generating a magnetic drive field in direction of the y-axis are controlled. The first drive field coil is controlled with a first drive field current having the form $I_x = \hat{I}_x \sin(\omega_x t)$, wherein $\hat{I}_x$ is a first drive field amplitude and $\omega_x$ is a first drive field frequency. The second drive field coil is controlled with a second drive field current having the form $I_y = \hat{I}_y \sin(\omega_y t)$, wherein $\hat{I}_y$ is a second drive field amplitude and $\omega_y$ is a second drive field frequency. For receiving closed Lissajous curves the frequency ratio of both drive field frequencies has to be rational. Advantageously, both drive field frequencies fulfill the frequency ratio condition $$\frac{\omega_x}{\omega_y} = \frac{N+1}{N}.$$

The closed 2D Lissajous curve lies within the x-y-plane. Of course appropriate closed 2D Lissajous curves in any other plane may be generated by appropriate currents flowing through the corresponding drive field coils. Advantageously the 2D Lissajous curve existing in the x-y-plane is moved in z-direction by creating an appropriate magnetic focus field, resulting in a 3D trajectory.

The frequency ratio for the closed Lissajous curve having a low density is greater than the frequency ratio for a (conventional) closed Lissajous curve having a high density. For example the following frequency ratios are chosen:

$$\frac{\omega_x}{\omega_y} = \frac{10}{9}$$

for the Lissajous curve used having a low density, whereas a Lissajous curve having a high density has a frequency ratio of e.g.

$$\frac{\omega_x}{\omega_y} = \frac{100}{99}.$$

Two frequencies $f_x$ and $f_y$ (where $2\pi f = \omega$) of a 2D Lissajous curve thus have the relationship $$f_y = \frac{N}{N-1} f_x.$$

The Lissajous curve can thus be described by $L(t) := \begin{pmatrix} \sin\pi(f 2_x t) \\ \sin\pi(f 2_y t) \end{pmatrix}$.

The repetition time for the curve is $T_R = (N-1)\frac{1}{f_x} = N\frac{1}{f_y}$.

If N is large, a high density trajectory is obtained, if N is small, a low density trajectory is obtained. Exemplary values are provided in the following table.

| $f_x$ | N | $f_y$ | $T_R$ |
|---|---|---|---|
| 25.000 Hz | 100 | 25.252.5 Hz | 99 * 0.4 ms = 39.6 ms |
| 25.000 Hz | 10 | 27.777.8 Hz | 9 * 0.4 ms = 3.6 ms |

Figure 5A:
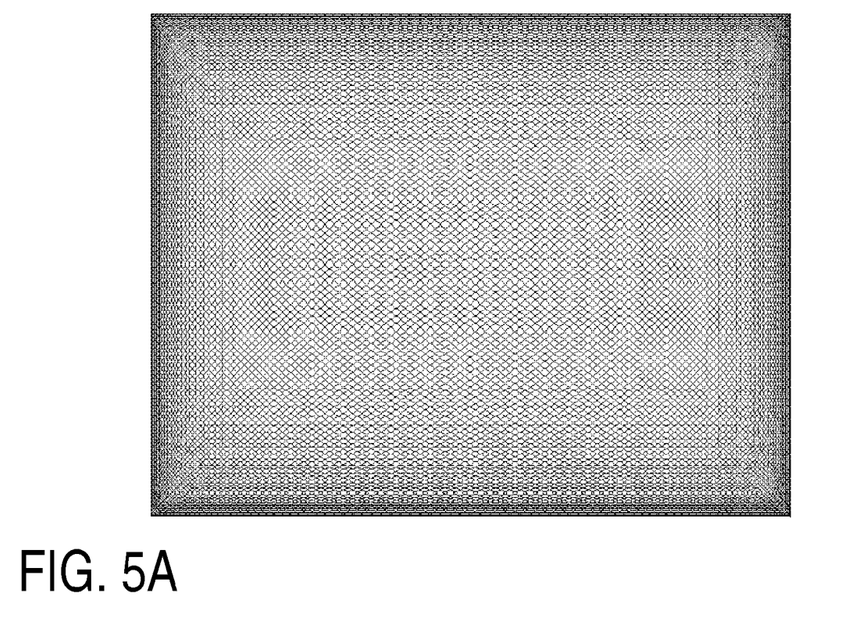
FIG. 5 shows a high density trajectory and a low density trajectory.
Figure 5B:
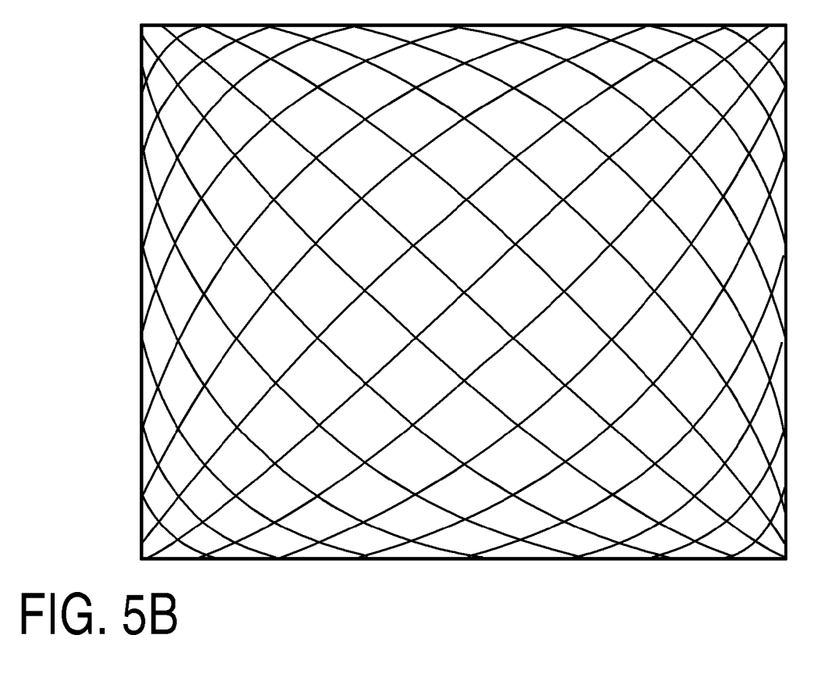

FIG. 5A shows a high density trajectory for N=100, and FIG. 5B shows a low density trajectory for N=10. In this example the high density trajectory is 11 times longer than the low density trajectory:

$$\frac{T_{R,NI=00}}{T_{R,NI=0}} = \frac{39,6 \text{ ms}}{3,9 \text{ ms}} = 11.$$

If the phases of at least one current is modified different trajectories are obtained:

$$L_p(t, \varphi) := \begin{pmatrix} \sin\pi(f 2_x t) \\ \sin\pi f_y(t\_2\varphi) \end{pmatrix}.$$

Here, for the phase $\varphi$ it holds with $p \in [1,P]$:

$$\varphi = 360° \frac{(p-1)}{P}.$$

In the example with P=11 it thus holds for the phase $\varphi$:

| | P | | | | | | | | | | |
|---|---|---|---|---|---|---|---|---|---|---|---|
| | 1 | 2 | 3 | 4 | 5 | 6 | 7 | 8 | 9 | 10 | 11 |
| Φ | 0° | 32.7° | 65.5° | 98.2° | 130.9° | 163.6° | 196.4° | 229.1° | 261.8° | 294.5° | 327.3° |

Figure 6:
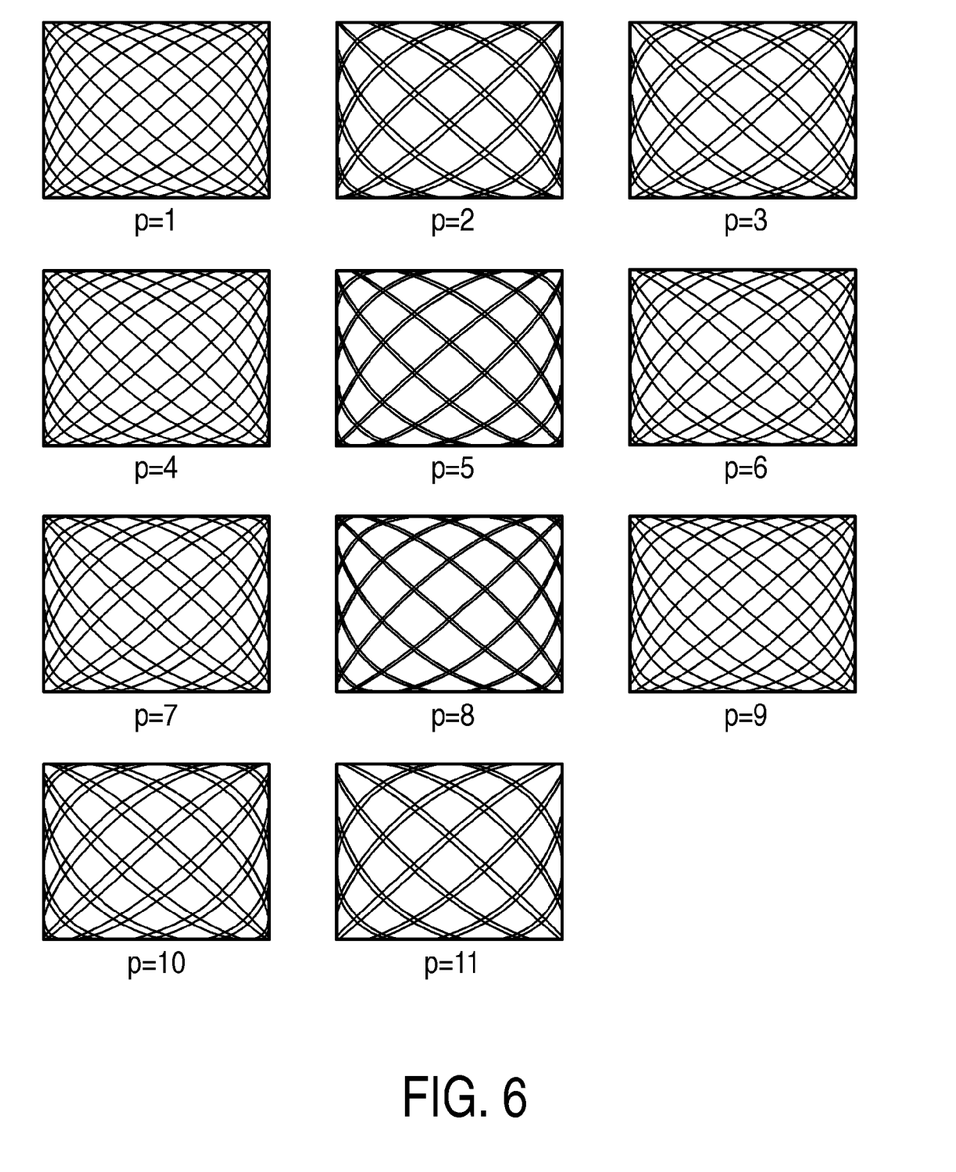
FIG. 6 shows a number of low density trajectories with different phases and different frequencies.
Figure 7:
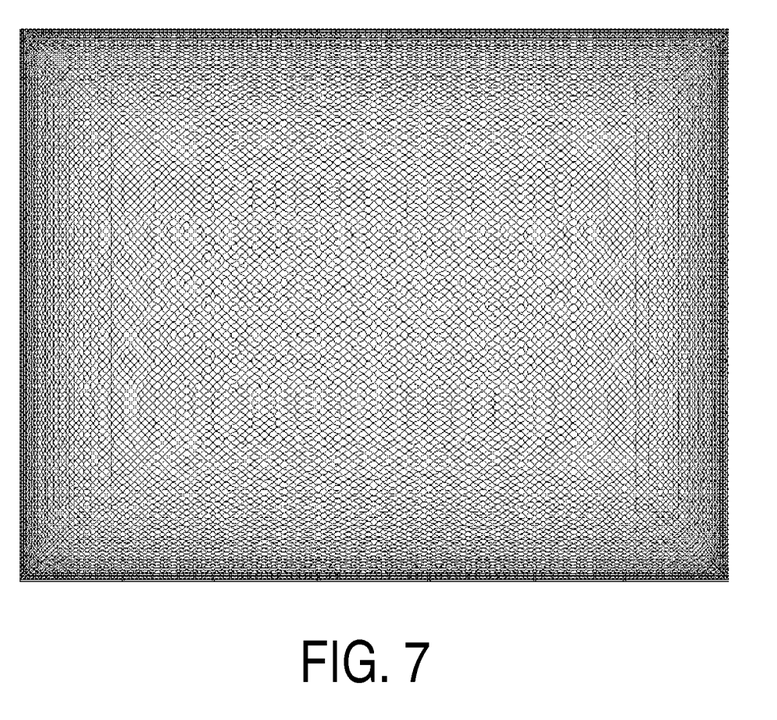
FIG. 7 shows a superposition of a number of low density trajectories shown in FIG. 6.

FIG. 6 shows a number of Lissajous curves having identical frequencies but different phases. If these trajectories are run through subsequently by the FFP, a total repetition time that equals the repetition time of a single high density trajectory is obtained, and the superposition of the Lissajous curves shown in FIG. 6 is depicted in FIG. 7. The result is a total trajectory having the same (or a similar) high density as the high density trajectory for N=100. But the trajectories are not equal. The trajectory for N=100 is a single closed curve, the travelling phase trajectory, i.e. the trajectory proposed according to the present invention (comprising a number of low density trajectories with different phases) shown in FIG. 7 is a superposition of a plurality p (here 11) of closed curves.

It is also possible to select the frequencies of the drive field currents to be identical (e.g. $f_x=f_y=25.000$ Hz). In this case the repetition time of a single closed curve (low density trajectory) is $T_R=0.4$ ms. This low density trajectory is shorter by a factor of P=99 than the high density trajectory. To avoid that the single low density trajectories are identical, it holds for the phases φ with p∈[1,P]:

$$\varphi = 180° \frac{(p-1)}{(P-1)}.$$

In the example with P=99 it holds (not all values are shown):

| | | | | | | p | | | | | | |
|---|---|---|---|---|---|---|---|---|---|---|---|---|
| | 1 | 10 | 19 | 28 | 37 | 46 | 55 | 64 | 73 | 82 | 91 | 99 |
| φ | 0° | 16.5° | 33.1° | 49.6° | 66.1° | 82.7° | 99.2° | 115.7° | 132.2° | 148.8° | 165.3° | 180° |

Figure 8:
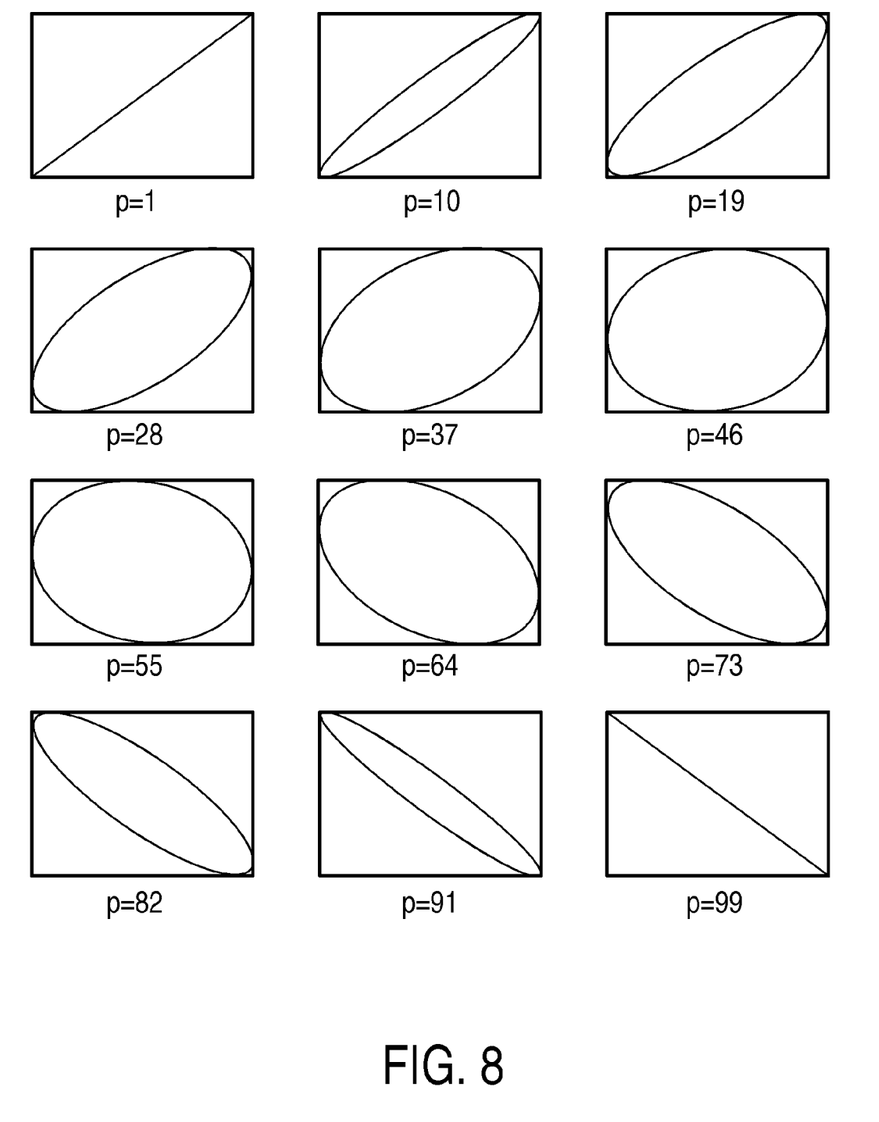
FIG. 8 shows a number of low density trajectories with different phases and identical frequencies.
Figure 9:
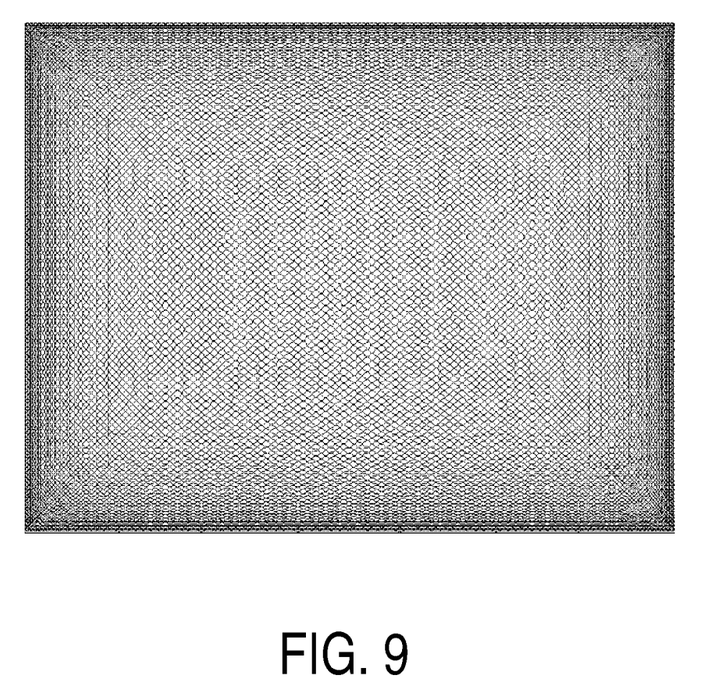
FIG. 9 shows a superposition of a number of low density trajectories shown in FIG. 8.

A few of these low density trajectories are shown in FIG. 8. A superposition of these trajectories results in a high density trajectory as shown in FIG. 9.

The proposed invention allows for selecting a small base repetition time and generating almost arbitrary dense trajectories by acquiring multiple repetitions with a travelling phase. As a result even identical frequencies can be chosen for setting up an MPI system. The freedom of choice of densities can, for instance, be used to have a fast orientation scan and subsequently a high resolution scan (by use of a conventional high density trajectory or by use of a number of low density trajectories with travelling phase). The present invention thus overcomes an essential limitation of the fixed (conventional) trajectory. Moreover, the proposed travelling phase trajectory can be used in a fixed mode without any disadvantages.

The present invention is not limited to 2D trajectories, but can also be applied for 3D trajectories. In this case the relationship between the three frequencies is, for instance:

$$f_y = \frac{N}{N-1} f_x \text{ and } f_z = \frac{N}{N+1} f_x$$

wherein N is an integer that is dividable by two.

Further, the present invention is not limited to the use of Lissajous trajectories, but generally any kind of trajectory can be used that has the form of a closed curve and whose superposition results in a high density sampling of the field of view (or the area of interest within the field of view).

The elements of the MPI apparatus that must be present for carrying out the invention much depend on the desired application. For instance, if no imaging shall be made with the MPI apparatus, but, for instance, if a desired region shall be heated for a hypothermia application, no receive coils and image processing means are required. Further, if only a small object shall be imaged (or heated) no focus means for changing the position in space of the field of view are necessarily required. Further modifications of the general layout of the MPI apparatus are possible as well.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. An apparatus for influencing magnetic particles in a field of view, which apparatus comprises:
    selection means comprising a selection field signal generator unit and selection field elements for generating a magnetic selection field having a pattern in space of its magnetic field strength such that a first sub-zone having a low magnetic field strength and a second sub-zone having a higher magnetic field strength are formed in the field of view,
    drive means comprising drive field signal generator units and drive field coils for changing the position in space of the two sub-zones in the field of view by means of a magnetic drive field so that the magnetization of the magnetic material changes locally, and
    control means for controlling said drive field signal generator units to generate drive currents for causing the drive field coils to generate a magnetic drive field such that the first sub-zone moves along a number p of predetermined low density trajectories each having the form of a closed curve differently located within the field of view, wherein each drive current has a drive current frequency and a drive current phase,
    wherein the drive currents are generated such that their drive current frequencies are equal or have a frequency ratio in the range from 0.5 to 0.98 and that the drive current phases of at least one drive current are different for the plurality p of low density trajectories, resulting in a high density sampling of the field of view by said first sub-zone after movement along said number p of predetermined low density trajectories.

2. An apparatus as claimed in claim 1,
wherein said drive currents are orthogonal sinusoidal drive currents.

3. An apparatus as claimed in claim 1,
wherein said drive currents $I_i$ are of the form $I_i=\hat{I}_i \sin(2\pi f_i t + \phi_i)$, wherein $\hat{I}_i$ is a the drive current amplitude, $\phi_i$ is the drive current phase, $f_i$ is drive field frequency and i indicates the direction of the magnetic drive field caused by the drive field coil provided with drive current $I_i$, wherein the drive current frequencies $f_i$ are all equal or wherein the drive current frequencies $$\frac{f_1}{f_2}$$

have a first frequency ratio of $$\frac{N-1}{N}$$

and the drive current frequencies $$\frac{f_3}{f_1}$$

have a second frequency ratio of $$\frac{N}{N+1},$$

N being a positive integer smaller than 50, in particular smaller than 20.

4. An apparatus as claimed in claim 1, wherein the predetermined low density trajectories have the form of Lissajous curves.

5. An apparatus as claimed in claim 1,
wherein the number p of predetermined low density trajectories is larger than 2, in particular larger than 10.

6. An apparatus as claimed in claim 1,
wherein the number p of predetermined low density trajectories is in the range from 10 to 200, in particular in the range from 50 to 100.

7. An apparatus as claimed in claim 3,
wherein the drive current phases $\phi_i$ of at least one drive current $I_i$ are distributed, in particular equally distributed, over the phase range from 0° to 360° for the number p of predetermined low density trajectories.

8. An apparatus as claimed in claim 1,
further comprising focus means comprising a focus field signal generator unit and focus field coils for changing the position in space of the field of view by means of a magnetic focus field.

9. An apparatus as claimed in claim 1,
further comprising
receiving means comprising at least one signal receiving unit and at least one receiving coil for acquiring detection signals, which detection signals depend on the magnetization in the field of view, which magnetization is influenced by the change in the position in space of the first and second sub-zone, and
processing means for processing said detection signals, in particular for reconstructing an image from said detection signals and/or for localizing said magnetic particles within the field of view, in particular within an object placed within the field of view.

10. A method for influencing magnetic particles in a field of view, which method comprises the steps of:
generating a magnetic selection field having a pattern in space of its magnetic field strength such that a first sub-zone having a low magnetic field strength and a second sub-zone having a higher magnetic field strength are formed in the field of view,
changing the position in space of the two sub-zones in the field of view by means of a magnetic drive field so that the magnetization of the magnetic material changes locally, and
generating drive currents for causing the drive field coils to generate a magnetic drive field such that the first sub-zone moves along a number p of predetermined low density trajectories each having the form of a closed curve differently located within the field of view, wherein each drive current has a drive current frequency and a drive current phase,
wherein the drive currents are generated such that their drive current frequencies are equal or have a frequency ratio in the range from 0.5 to 0.98 and that the drive current phases of at least one drive current are different for the plurality p of low density trajectories, resulting in a high density sampling of the field of view by said first sub-zone after movement along said number p of predetermined low density trajectories.

11. A non-transitory computer readable storage medium comprising a computer program, wherein the computer readable program when executed on a computer causes the computer to control an apparatus:
by a selection field signal generator unit and selection field elements of the apparatus, to generate a magnetic selection field having a pattern in space of its magnetic field strength such that a first sub-zone having a low magnetic field strength and a second sub-zone having a higher magnetic field strength are formed in the field of view,
by drive field signal generator units and drive field coils of the apparatus, to change a position in space of the two sub-zones in the field of view by means of a magnetic drive field so that the magnetization of the magnetic material changes locally, and
by said drive field signal generator units, to generate drive currents for causing the drive field coils to generate a magnetic drive field such that the first sub-zone moves along a number p of predetermined low density trajectories each having the form of a closed curve differently located within the field of view, wherein each drive current has a drive current frequency and a drive current phase,
wherein the drive currents are generated such that their drive current frequencies are equal or have a frequency ratio in the range from 0.5 to 0.98 and that the drive current phases of at least one drive current are different for the plurality p of low density trajectories, resulting in a high density sampling of the field of view by said first sub-zone after movement along said number p of predetermined low density trajectories.

* * * * *